(12) United States Patent
Howard et al.

(10) Patent No.: US 9,500,611 B2
(45) Date of Patent: Nov. 22, 2016

(54) LAMP ASSEMBLY FOR A THERMOGRAPHIC NONDESTRUCTIVE EVALUATION SYSTEM

(71) Applicant: General Electric Company, Schenectady, NY (US)

(72) Inventors: Donald Robert Howard, Troy, NY (US); Harry Israel Ringermacher, Delanson, NY (US); Waseem Ibrahim Faidi, Schenectady, NY (US); Bryon Edward Knight, Charlton, NY (US)

(73) Assignee: General Electric Company, Niskayuna, NY (US)

( * ) Notice: Subject to any disclaimer, the term of this patent is extended or adjusted under 35 U.S.C. 154(b) by 559 days.

(21) Appl. No.: 14/037,621

(22) Filed: Sep. 26, 2013

(65) Prior Publication Data

US 2015/0085895 A1 Mar. 26, 2015

(51) Int. Cl.
*G01N 25/72* (2006.01)

(52) U.S. Cl.
CPC .................... *G01N 25/72* (2013.01)

(58) Field of Classification Search
CPC .... G01N 25/72; G01N 21/00; G01N 21/474; G01N 2021/4752; G01N 2021/4783; G01N 2021/6469
USPC ............................................................ 374/5
See application file for complete search history.

(56) References Cited

U.S. PATENT DOCUMENTS

| 5,179,677 A | 1/1993 | Anderson et al. |
| 5,711,603 A | 1/1998 | Ringermacher et al. |
| 6,367,969 B1 | 4/2002 | Ringermacher et al. |
| 6,394,646 B1 | 5/2002 | Ringermacher et al. |
| 6,542,849 B2 | 4/2003 | Sun |
| 7,549,789 B2 | 6/2009 | Tralshawala et al. |
| 7,805,251 B2 | 9/2010 | Ringermacher et al. |
| 8,055,054 B2 | 11/2011 | Ringermacher et al. |
| 8,393,784 B2 | 3/2013 | Ringermacher et al. |
| 2002/0110176 A1* | 8/2002 | Sun ........................ G01N 25/72 374/5 |
| 2002/0126730 A1 | 9/2002 | Sun et al. |
| 2002/0128797 A1 | 9/2002 | Sun |
| 2005/0018748 A1 | 1/2005 | Ringermacher et al. |

(Continued)

FOREIGN PATENT DOCUMENTS

| EP | 0089760 | 9/1983 |
| JP | 2004117194 A | 4/2004 |

OTHER PUBLICATIONS

Milne et al., "Application of Thermal Pulses and Infrared Thermal Imagers for Observing Sub-surface Structures in Metals and Composites," SPIE Proceedings, Infrared Technology and Applications, vol. 0590, May 1, 1986, pp. 293-302.

(Continued)

*Primary Examiner* — Lisa Caputo
*Assistant Examiner* — Philip Cotey
(74) *Attorney, Agent, or Firm* — Nitin N. Joshi

(57) ABSTRACT

A thermographic nondestructive evaluation system includes a lamp assembly having a lamp. The lamp is configured to be positioned within an internal cavity of a target object and to emit an energy pulse toward an interior surface of the internal cavity. The lamp includes at least one curved portion, the at least one curved portion is curved relative to a longitudinal axis of the lamp, and a first curvature of the curved portion is selected to substantially correspond to a second curvature of the internal cavity.

20 Claims, 3 Drawing Sheets

(56) References Cited

U.S. PATENT DOCUMENTS

| | | |
|---|---|---|
| 2005/0207468 A1 | 9/2005 | McCullough et al. |
| 2008/0144049 A1 | 6/2008 | Ringermacher et al. |
| 2010/0044589 A1* | 2/2010 | Garcia .................. F21V 29/20 250/492.1 |
| 2012/0050537 A1 | 3/2012 | Ringermacher et al. |

OTHER PUBLICATIONS

Buchanan et al., "Recent Advances in Digital Thermography for Nondestructive Evaluation," SPIE Proceedings, Thermosense Xii: An International Conference on Thermal Sensing and Imaging Diagnostic, vol. 1313, Mar. 1, 1990, pp. 134-142.

Daniels, "Preliminary Design of the Portable Thermal Nondestructive Evaluation System," PSR Report 2708, 1997, pp. 1-19.

Maldague et al., "A Study of Defect Depth Using Neural Networks in Pulsed Phase Thermography: Modeling, Noise, Experiments," Rev. Gen Therm., 1998, vol. 37, pp. 704-717.

Ringermacher et al., "Discriminating Porosity in Composites Using Thermal Depth Imaging," AIP Conference Proceedings, vol. 615, 2001, pp. 528-535.

Santulli, "Impact Damage Characterisation of Thermoplastic Matrix Composites Using Transmission Transient Thermography," Nondestructive Testing and Evaluation, vol. 19, Issue 3, 2003, pp. 79-90.

Burrows et al., "Combined Laser Spot Imaging Thermography and Ultrasonic Measurements for Crack Detection," Nondestructive Testing and Evaulation, vol. 22, Issue 2-3, 2007, pp. 217-227.

PCT Search Report issued in connection with corresponding WO Patent Application No. PCT/US2014/054871 dated on Jan. 12, 2015.

\* cited by examiner

LAMP ASSEMBLY FOR A THERMOGRAPHIC NONDESTRUCTIVE EVALUATION SYSTEM

BACKGROUND

The subject matter disclosed herein relates to a lamp assembly for a thermographic nondestructive evaluation system.

Infrared (IR) transient thermography is a nondestructive testing technique that utilizes temporal measurements of heat transference through an object to provide information concerning the structure and integrity of the object. Because heat flow through an object is substantially unaffected by the micro-structure and the single-crystal orientations of the material of the object, an infrared transient thermography analysis is essentially free of the limitations this creates for ultrasonic measurements. In contrast to most ultrasonic techniques, a transient thermographic analysis approach is not significantly hampered by the size, contour, or shape of the object being tested and, moreover, can be accomplished ten to one hundred times faster than most conventional ultrasonic methods when testing objects of large surface area.

Conventionally, an infrared (IR) video camera is used to record and store successive thermal images (frames) of an object surface after heating. Each video image is composed of a fixed number of pixels. In this context, a pixel is a small picture element in an image array or frame, which corresponds to a rectangular area, called a resolution element, on the surface of the object being imaged. Because the temperature at each resolution element is directly related to the intensity of the corresponding pixel, temperature changes at each resolution element on the object surface may be analyzed in terms of changes in pixel contrast. One known contemporary application of transient thermography is to determine the size and relative location (depth) of flaws within solid non-metal composites. Another application of transient thermography is for determining the thickness of metal objects.

Certain transient thermography systems employ a lamp to heat the target object prior to or during acquisition of the thermal images. For example, a lamp may be disposed within an internal cavity of a hollow object, such as a pipe or conduit. An IR video camera may be positioned outside the hollow object and configured to receive thermal images from the object after being heated by the lamp. Unfortunately, due to the shape and/or size of certain internal cavities, typical lamps may be unable to fit within the target object. Accordingly, such objects may be unsuitable for evaluation by a transient thermography system.

BRIEF DESCRIPTION

In one embodiment, a thermographic nondestructive evaluation system includes a lamp assembly having a lamp. The lamp is configured to be positioned within an internal cavity of a target object and to emit an energy pulse toward an interior surface of the internal cavity. The lamp includes at least one curved portion, the at least one curved portion is curved relative to a longitudinal axis of the lamp, and a first curvature of the curved portion is selected to substantially correspond to a second curvature of the internal cavity.

In another embodiment, a thermographic nondestructive evaluation system includes a lamp assembly having a lamp and a self-contained power supply. The lamp is configured to be positioned within an internal cavity of a target object and to emit an energy pulse toward an interior surface of the internal cavity, and the self-contained power supply is configured to supply the lamp with sufficient electrical power to emit the energy pulse.

In a further embodiment, a thermographic nondestructive evaluation system includes a lamp assembly having a lamp and a mounting assembly. The lamp is configured to be positioned within an internal cavity of a target object and to emit an energy pulse toward an interior surface of the internal cavity, and the mounting assembly is configured to selectively couple the lamp to the target object.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
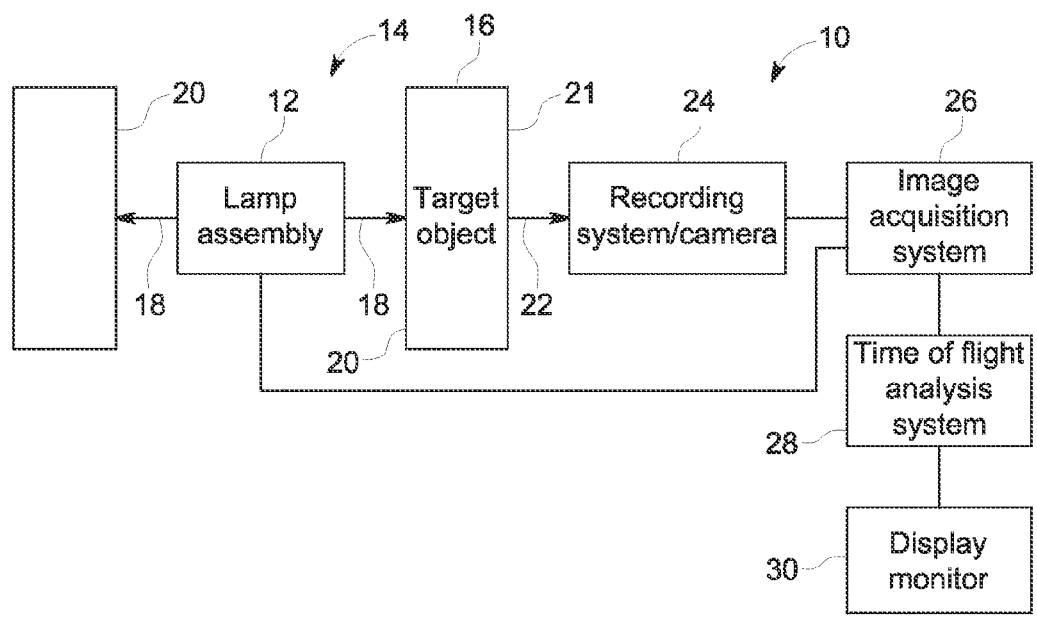
FIG. 1 is a block diagram of an embodiment of a thermographic nondestructive evaluation system.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments disclosed herein, the articles "a," "an," "the," and "said" are intended to mean that there are one or more of the elements. The terms "comprising," "including," and "having" are intended to be inclusive and mean that there may be additional elements other than the listed elements.

Embodiments disclosed herein may enhance energy transfer from a lamp of a thermographic nondestructive evaluation system to a target object by particularly positioning the lamp within an internal cavity of the target object and/or particularly shaping the lamp to match the contours of the internal cavity. In certain embodiments, a thermographic nondestructive evaluation system includes a lamp assembly having a lamp configured to be positioned within an internal cavity of a target object and to emit an energy pulse toward an interior surface of the internal cavity. The lamp includes at least one curved position, the at least one curved position is curved relative to a longitudinal axis of the lamp, and a first curvature of the curved position is selected to substantially correspond to a second curvature of the internal cavity. By selecting a lamp shape based on the shape of the internal cavity, an exterior surface of the lamp may be positioned proximate to the interior surface of the internal cavity, thereby enhancing energy transfer from the lamp to the interior surface. In certain embodiments, a cross-sectional area of the lamp and/or a cross-sectional shape of the lamp is selected based at least in part on an inner cross-sectional area and/or an inner cross-sectional shape of the internal cavity. Selecting the cross-sectional area/shape of the lamp based on the inner cross-sectional area/shape of the internal cavity may further enhance energy transfer from the lamp to the target object. In further embodiments, the lamp assembly includes a mounting assembly configured to selectively couple the lamp to the target object. A support structure extending between the mounting assembly and the lamp is configured to position the lamp in a desired location relative to the target object. By positioning the lamp at the desired location, the energy pulse from the lamp may be efficiently transferred to a portion of the target object being monitored, thereby enhancing the efficiency and/or the accuracy of the thermographic nondestructive evaluation system.

FIG. 1 is a block diagram of an embodiment of a thermographic nondestructive evaluation system 10 for detecting flaws in a target object. As discussed in detail below, the thermographic nondestructive evaluation system 10 includes a lamp assembly 12 having a lamp configured to be disposed within an internal cavity 14 of the target object 16. The target object 16 may be any suitable industrial part having an internal cavity, such as a combustion liner, a shroud, a conduit, a pipe, or a similar part (e.g., for a gas turbine engine system or for an aircraft system). The lamp (e.g., a flash lamp, a light emitting diode assembly, etc.) of the lamp assembly 12 is configured to emit an energy pulse 18 (e.g., optical pulse, heat pulse, etc.) toward an interior surface 20 of the internal cavity 14. In certain embodiments, the lamp may rapidly apply multiple high-power energy pulses 18 toward the interior surface 20. Once the energy pulse 18 or multiple energy pulses 18 are applied to the interior surface 20, a thermal pulse or multiple thermal pulses propagate through the target object 16 and radiate from an exterior surface 21 as thermal radiation 22.

In the illustrated embodiment, the thermographic nondestructive evaluation system 10 includes a recording system or camera 24 configured to collect the thermal radiation 22 from the exterior surface 21 of the target object 16. The thermal radiation 22 includes data representative of the propagation and evolution of the thermal pulse/pulses through the target object 16. In certain embodiments, the recording system or camera 24 includes a high-speed infrared (IR) focal plane array camera for monitoring the temperature and/or for imaging the thermal profile of the target object 16. In the illustrated embodiment, the lamp of the lamp assembly 12 is disposed within the internal cavity 14 of the target object 16, and the recording system/camera 24 is positioned outside the target object 16. In this configuration, energy pulses emitted by the lamp propagate through the target object 16 and are captured by the recording system/camera 24. In certain embodiments, the recording/ system camera 24 utilizes an IR transient thermography imaging method to receive and capture images of the thermal radiation 22, which represents the propagation of the thermal pulses through the target object 16. The images include temperature-time responses (also referred to as T-t curves) at different points along the exterior surface 21 of the target object 16.

The thermographic nondestructive evaluation system 10 also includes an image acquisition system 26 that is communicatively coupled to the recording system/camera 24 and to the lamp assembly 12 (e.g., via wired and/or wireless communication links). In certain embodiments, the image acquisition system 26 may be included within the recording system/camera 24. Acquisition of the thermal radiation 22 may be initiated concurrently with activation of the lamp, either by optical triggering or by other suitable triggering systems. Activation of the lamp is controlled by electrical circuitry within the image acquisition system 26 and/or within the lamp assembly 12. In certain embodiments, lamp activation is managed by video frame acquisition software, which may be executed on a computer system or a processor, such as within a time of flight analysis system 28.

The time of flight analysis system 28 is configured to capture image data from the image acquisition system 26. The time of flight analysis system 28 is also configured to analyze the data, and to determine thickness values at different points along the target object 16, thereby facilitating detection of flaws within the target object. In addition, the time of flight analysis system 28 normalizes temperature variability in the time-temperature responses while processing the time-dependence of the temperature field of the images. In certain embodiments, the time of flight analysis system 28 is configured to use an inflection point in time of the time-temperature responses at each pixel to determine thickness and diffusivity values corresponding to different points in the target object 16.

In the illustrated embodiment, the thermographic nondestructive evaluation system 10 includes a display monitor 30, which is configured to receive output signals from the time of flight analysis system 28. The display monitor 30 is configured to present visual data to a user based on the output signals. The visual data may be representative of the thickness profile and/or the detected flaws within the target object 16. In certain embodiments, the display monitor 30 may be connected to a printer or to another suitable device for displaying the output from the time of flight analysis system 28. For example, the thermographic nondestructive evaluation system 10 may detect shadows due to bubbles, delaminations, and/or other flaws within the target object 16, and display an accurate representation of the position of such flaws on the display monitor 30. In certain embodiments, the display monitor 30 presents a visual representation of thermal diffusivity as a function of location throughout the target object 16, thereby facilitating measurement of local thickness and detection of flaws.

Figure 2:
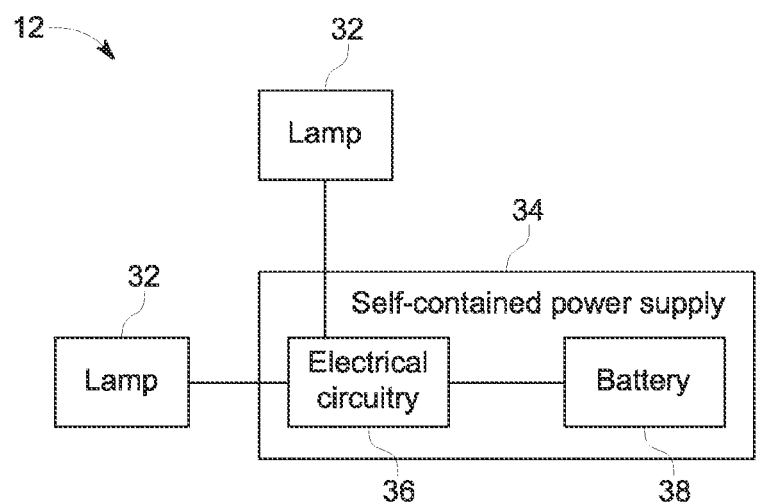
FIG. 2 is a block diagram of an embodiment of a lamp assembly that may be employed within the thermographic nondestructive evaluation system of FIG. 1.

FIG. 2 is a block diagram of an embodiment of a lamp assembly 12 that may be employed within the thermographic nondestructive evaluation system 10 of FIG. 1. In the illustrated embodiment, the lamp assembly 12 includes two lamps 32 and a self-contained power supply 34. As previously discussed, each lamp 32 is configured to be positioned within an internal cavity of a target object and to emit an energy pulse toward an interior surface of the internal cavity. For example, in certain embodiments, the lamp may include at least one flash lamp configured to emit a pulse of optical and/or thermal energy. In alternative embodiments, the lamp may include one or more other suitable optical and/or thermal energy emitters, such as a light emitting diode (LED), a fluorescent bulb, or an incandescent bulb, for example. In further embodiments, the lamp may include a device configured to emit pulses of infrared radiation, ultraviolet radiation, visible radiation, radio frequency radiation, and/or x-ray radiation, among other radiation within the electromagnetic spectrum.

In certain embodiments, each lamp 32 is disposed within the same internal cavity and configured to emit energy pulses toward a respective region of the internal cavity. In alternative embodiments, a first lamp may be disposed within a first internal cavity and the second lamp may be disposed within a second internal cavity. For example, each internal cavity may be a component of a single target object, and the lamps may be configured to emit energy pulses toward respective regions of the target object. Alternatively, each internal cavity may be associated with a separate target object. While the illustrated lamp assembly 12 includes two lamps 32, it should be appreciated that alternative lamp assemblies 12 may include more or fewer lamps 32. For example, in certain embodiments, the lamp assembly 12 may include 1, 2, 3, 4, 5, 6, 7, 8, or more lamps 32.

As illustrated, each lamp 32 is communicatively coupled to the self-contained power supply 34. The self-contained power supply 34 is configured to supply each lamp 32 with sufficient electrical power to emit respective energy pulses. In the illustrated embodiment, the self-contained power supply 34 includes electrical circuitry 36 and a battery 38. The battery 38 may include any suitable device configured to supply the lamps 32 with electrical power, such as a rechargeable battery or a replaceable battery. The electrical circuitry 36 is configured to control operation of the lamps 32. For example, in certain embodiments, the image acquisition system 26 is configured to send a signal (e.g., via a wired or wireless connection) to the electrical circuitry 36 within the self-contained power supply 34 that instructs the lamp 32 to activate. The electrical circuitry 36, in turn, is configured to direct electrical power from the battery 38 to the lamp 32 upon receiving the signal, thereby activating the lamp 32.

In certain embodiments, the self-contained power supply 34 is coupled to the lamps 32 and configured to be positioned within the internal cavity of the target object. In such embodiments, each component of the lamp assembly 12 may be disposed within a common housing, thereby forming a unitary assembly. In alternative embodiments, the self-contained power supply 34 is configured to be positioned proximate to the target object and electrically coupled to the lamps 32. As previously discussed, the self-contained electrical power supply 34 is configured to supply the lamps 32 with sufficient electrical power to emit the respective energy pulses. Accordingly, an electrical connection between the lamps and an external power supply is obviated. As a result, the duration and costs associated with installing the lamps within the internal cavity of the target object may be substantially reduced.

Figure 3:
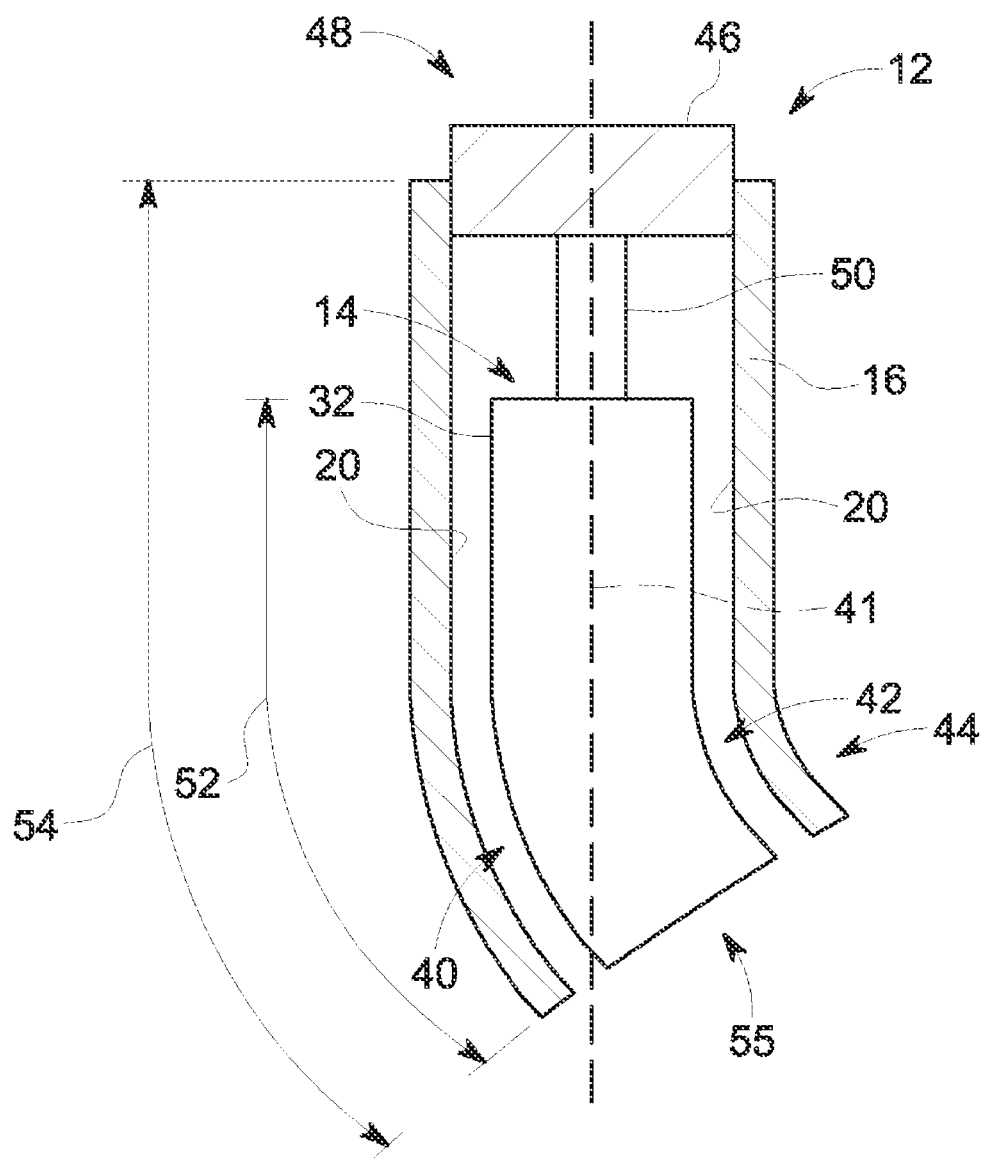
FIG. 3 is a cross-sectional view of an embodiment of a lamp assembly having a lamp positioned within an internal cavity of a target object.

FIG. 3 is a cross-sectional view of an embodiment of a lamp assembly 12 having a lamp 32 positioned within an internal cavity 14 of a target object 16. In certain embodiments, the lamp 32 is particularly configured to correspond to the size and/or shape of the internal cavity 14. For example, in the illustrated embodiment, the lamp 32 includes a curved portion 40, which is curved relative to a longitudinal axis 41 of the lamp 32. A first curvature 42 (e.g., radius of curvature, direction of curvature, etc.) of the curved portion 40 is selected to substantially correspond to a second curvature 44 of the internal cavity 14, thereby enabling the lamp 32 to substantially match the contours of the internal cavity 14. By selecting a lamp shape that matches the shape of the internal cavity 14, an exterior surface of the lamp may be positioned proximate to the interior surface 20 of the internal cavity 14, thereby enhancing energy transfer from the lamp to the target object. In addition, the selected lamp shape may facilitate insertion and removal of the lamp from the internal cavity.

While the illustrated curved portion 40 forms a simple curve (e.g., a one-dimensional curve) that substantially corresponds to the curvature 44 of the internal cavity 14, it should be appreciated that the lamp 32 may include a curved portion that forms a compound curve (e.g., a two-dimensional curve) that substantially corresponds to a compound curved internal cavity 14. For example, in certain embodiments, the curved portion 40 of the lamp 32 may be curved in multiple directions relative to the longitudinal axis 41. In further embodiments, the lamp 32 may include multiple curved portions that match the contours of an internal cavity having multiple curved regions. By way of example, the lamp 32 may include 1, 2, 3, 4, 5, 6, 7, 8, or more curved portions, each forming a simple or compound curve.

In the illustrated embodiment, the lamp assembly 12 includes a mounting assembly 46 configured to selectively couple the lamp 32 to the target object 16. As illustrated, the mounting assembly 46 is configured to selectively couple to an opening 48 in the target object 16. For example, in certain embodiments, the interior surface 20 of the internal cavity 14 includes threads configured to interface with corresponding threads of the mounting assembly 46. In such embodiments, the lamp 32 may be inserted into the internal cavity 14, and the mounting assembly 46, which supports the lamp 32, may be coupled to the opening 48 via a threaded connection. In alternative embodiments, the mounting assembly 46 may be clipped, adhesively bonded, press-fit, or otherwise attached to the opening 48 to couple the lamp 32 to the target object 16. In further embodiments, the mounting assembly 46 may be configured to selectively couple to other portions of the target object (e.g., the interior surface 20 of the internal cavity 14, etc.) and/or to a structure positioned proximate to the target object (e.g., a mounting base, etc.).

In the illustrated embodiment, the lamp assembly 12 includes a support structure 50 extending between the mounting assembly 46 and the lamp 32. The support structure 50 is configured to position the lamp 32 in a desired location relative to the target object 16. For example, in certain embodiments, the portion of the target object monitored by the thermographic nondestructive evaluation system 10 may be remote from the opening 48. In such embodiments, the support structure 50 may position the lamp 32 proximate to the monitored portion of the target object, thereby enabling the lamp 32 to emit an energy pulse toward the monitored portion. As a result, energy transfer efficiency between the lamp and the monitored portion of the target object may be enhanced. While the illustrated embodiment includes a support structure 50, it should be appreciated that the lamp 32 may be directly coupled to the mounting assembly 46 in alternative embodiments.

In the illustrated embodiment, a first length 52 of the lamp 32 is selected based on a second length 54 of the internal cavity 14. For example, as illustrated, the length 52 of the lamp 32 is selected such that the lamp extends to a second end 55 of the target object 16, opposite the opening 48. In certain embodiments, the length of the lamp may be selected to substantial correspond to the monitored portion of the target object. For example, the lamp 32 may emit an energy pulse along a length of the monitored portion of the target object, thereby enabling the thermographic nondestructive evaluation system to detect flaws within a desired region of the target object. As will be appreciated, longer lamps 32 and/or more lamps 32 may be utilized for target objects having longer monitored portions, and shorter lamps 32 or fewer lamps 32 may be utilized for target objects having shorter monitored portions. While the first length 52 of the illustrated lamp is less than the second length 54 of the internal cavity 14, it should be appreciated that, in alternative embodiments, the first length 52 may be greater than the second length 54.

Figure 4:
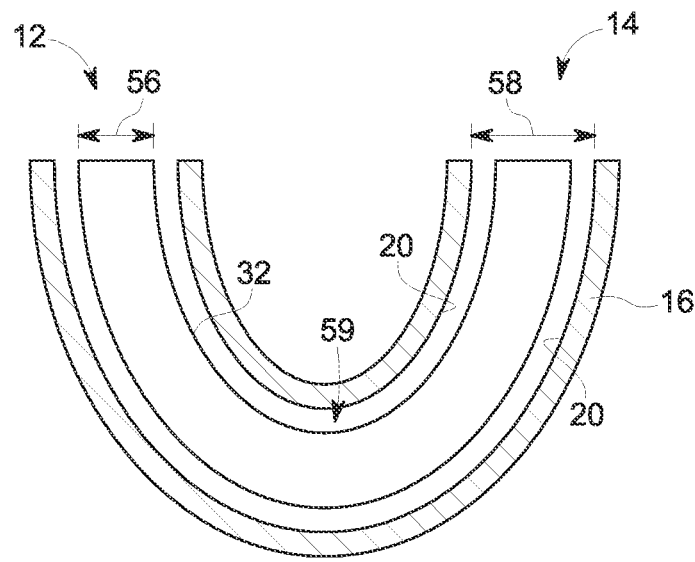
FIG. 4 is a cross-sectional view of another embodiment of a lamp assembly having a substantially u-shaped lamp.

FIG. 4 is a cross-sectional view of another embodiment of a lamp assembly 12 having a substantially u-shaped lamp 32. As illustrated, the shape of the lamp 32 substantially corresponds to the shape of the internal cavity 14, thereby enabling the lamp to emit an energy pulse along a length of the internal cavity 14. In addition, the curved shape of the lamp 32 enables the lamp to be inserted and removed from the target object. In certain embodiments, the internal cavity includes a substantially circular cross-section. In such embodiments, the lamp 32 may include a corresponding circular cross-section to substantially match the shape of internal cavity cross-section.

In certain embodiments, a cross-sectional area of the lamp 32 may be selected based at least in part on an inner cross-sectional area of the internal cavity 14. For example, if the lamp 32 and the internal cavity 14 have substantially circular cross-sections, a diameter 56 of the lamp 32 may be selected based on a diameter 58 of the internal cavity 14. The diameter 56 of the lamp may be less than the diameter 58 of the internal cavity 14 to facilitate insertion and removal of the lamp 32. In addition, the diameter 56 of the lamp 32 may be selected to position an outer surface 59 of the lamp 32 proximate to the interior surface 20 of the internal cavity 14 along the length of the target object 16. For example, the diameter 56 of the lamp 32 may be selected to establish a cross-sectional area that is greater than 50 percent, 60 percent, 70 percent, 80 percent, 90 percent, or more, of the cross-sectional area of the internal cavity 14. By way of example, the cross-sectional area of the lamp 32 may be about 50 percent to about 95 percent, or about 60 percent to about 90 percent, about 70 percent to about 80 percent of the cross-sectional area of the internal cavity 14.

Placing the outer surface 59 of the lamp 32 proximate to the interior surface 20 of the internal cavity 14 along the length of the target object 16 facilitates energy transfer from the lamp 32 to the target object 16, thereby enhancing the efficiency of the thermographic nondestructive evaluation system 10 and/or enhancing the battery life of the self-contained power supply, if employed. Furthermore, because the lamp 32 is shaped to match the contours of the internal cavity 14, the energy emitted by the lamp 32 may be substantially evenly distributed along the interior surface 20 of the internal cavity 14, thereby enhancing the accuracy of the thermographic nondestructive evaluation system 10. While the illustrated lamp 32 includes a substantially circular cross-sectional shape, it should be appreciated that the cross-sectional shape of the lamp 32 may be selected to substantially correspond to the inner cross-sectional shape of the internal cavity. For example, if the inner cross-sectional shape of the internal cavity is elliptical or polygonal, the cross-sectional shape of the lamp may be elliptical or polygonal.

Figure 5:
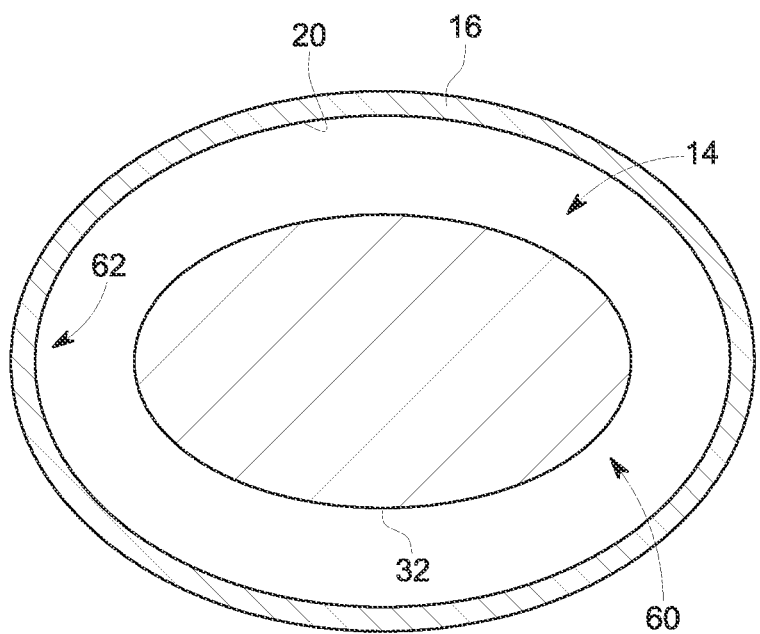
FIG. 5 is a cross-sectional view of a further embodiment of a lamp assembly having a lamp with an elliptical cross-section.

FIG. 5 is a cross-sectional view of a further embodiment of a lamp assembly 12 having a lamp 32 with an elliptical cross-section. As previously discussed, the cross-sectional area of the lamp 32 may be selected based at least in part on an inner cross-sectional area of the internal cavity 14. For example, the cross-sectional area of the lamp 32 may be selected such that the outer surface 59 of the lamp 32 is positioned proximate to the interior surface 20 of the target object 16, thereby enhancing energy transfer from the lamp 32 to the target object 16. In certain embodiments, a cross-sectional shape 60 of the lamp 32 is selected based at least in part on an inner cross-sectional shape 62 of the internal cavity 14. For example, in the illustrated embodiment, the elliptical cross-sectional shape 60 of the lamp 32 is selected to substantially correspond to the elliptical cross-sectional shape 62 of the internal cavity 14. Accordingly, energy emitted by the lamp 32 may be substantially evenly distributed along the interior surface 20 of the internal cavity 14. While the cross-sections of the lamp 32 and the internal cavity 14 are substantially elliptical in the illustrated embodiment, it should be appreciated that, in alternative embodiments, the lamp 32 and/or the internal cavity 14 may have a substantially circular or a substantially polygonal cross-sectional shape, among other suitable shapes.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A thermographic nondestructive evaluation system comprising:
a lamp assembly having a lamp configured to be positioned within an internal cavity of a target object and to emit an energy pulse toward an interior surface of the internal cavity, wherein the lamp includes at least one curved portion, the at least one curved portion is curved relative to a longitudinal axis of the lamp, and a first curvature of the curved portion is selected to substantially match a second curvature of the internal cavity.

2. The thermographic nondestructive evaluation system of claim 1, wherein the lamp is substantially u-shaped.

3. The thermographic nondestructive evaluation system of claim 1, wherein a cross-sectional area of the lamp is selected based at least in part on an inner cross-sectional area of the internal cavity.

4. The thermographic nondestructive evaluation system of claim 1, wherein a cross-sectional shape of the lamp substantially matches at least in part an inner cross-sectional shape of the internal cavity.

5. The thermographic nondestructive evaluation system of claim 1, wherein a first length of the lamp is selected based at least in part on a second length of the internal cavity.

6. The thermographic nondestructive evaluation system of claim 5, wherein the first length is less than the second length.

7. The thermographic nondestructive evaluation system of claim 1, wherein the lamp assembly comprises a support structure configured to position the lamp is a desired location relative to the target object.

8. The thermographic nondestructive evaluation system of claim 1, wherein the lamp assembly comprising:
a self-contained power supply configured to supply the lamp with sufficient electrical power to emit the energy pulse; and
a mounting assembly configured to selectively couple the lamp to the target object.

9. The thermographic nondestructive evaluation system of claim 1, comprising:
- a focal plane array camera configured to capture a plurality of images corresponding to evolution of heat due to an impact of the energy pulse on the target object; and
- an image acquisition system for capturing data corresponding to the plurality of images from the focal plane array camera.

10. The thermographic nondestructive evaluation system of claim 1, wherein the first curvature of the curved portion comprises a first radius of curvature and a first direction of curvature that is selected to substantially match a second radius of curvature and a second direction of curvature of the second curvature of the internal cavity.

11. A thermographic nondestructive evaluation system comprising:
- a lamp assembly having a lamp and a self-contained power supply, wherein the lamp is configured to be positioned within an internal cavity of a target object and to emit an energy pulse toward an interior surface of the internal cavity, and the self-contained power supply is configured to supply the lamp with sufficient electrical power to emit the energy pulse, wherein the lamp includes at least one curved portion, the at least one curved portion is curved relative to a longitudinal axis of the lamp, and a first curvature of the curved portion is selected to substantially match to a second curvature of the internal cavity.

12. The thermographic nondestructive evaluation system of claim 11, wherein the self-contained power supply comprises a battery and electrical circuitry configured to control operation of the lamp.

13. The thermographic nondestructive evaluation system of claim 11, wherein the lamp assembly comprises a support structure configured to position the lamp is a desired location relative to the target object.

14. The thermographic nondestructive evaluation system of claim 11, comprising a mounting assembly configured to selectively couple the lamp to the target object.

15. The thermographic nondestructive evaluation system of claim 11, wherein the first curvature of the curved portion comprises a first radius of curvature and a first direction of curvature that is selected to substantially match a second radius of curvature and a second direction of curvature of the second curvature of the internal cavity.

16. A thermographic nondestructive evaluation system comprising:
- a lamp assembly having a lamp and a mounting assembly, wherein the lamp is configured to be positioned within an internal cavity of a target object and to emit an energy pulse toward an interior surface of the internal cavity, and the mounting assembly is configured to selectively couple the lamp to the target object, wherein the lamp includes at least one curved portion, the at least one curved portion is curved relative to a longitudinal axis of the lamp, and a first curvature of the curved portion is selected to substantially match to a second curvature of the internal cavity.

17. The thermographic nondestructive evaluation system of claim 16, wherein the lamp assembly comprises a support structure extending between the mourning assembly and the lamp, and the support structure is configured to position the lamp in a desired location relative to the target object.

18. The thermographic nondestructive evaluation system of claim 16, wherein the mounting assembly is configured to selectively couple to an opening in the target object.

19. The thermographic nondestructive evaluation system of claim 16, wherein the lamp assembly comprises a self-contained power supply configured to supply the lamp with sufficient electrical power to emit the energy pulse.

20. The thermographic nondestructive evaluation system of claim 16, wherein the first curvature of the curved portion comprises a first radius of curvature and a first direction of curvature that is selected to substantially match a second radius of curvature and a second direction of curvature of the second curvature of the internal cavity.

* * * * *